(12) United States Patent
Olbert et al.

(10) Patent No.: US 9,012,707 B2
(45) Date of Patent: Apr. 21, 2015

(54) CONTINUOUS PROCESS FOR CARRYING OUT AUTOTHERMAL GAS-PHASE DEHYDROGENATIONS

(75) Inventors: Gerhard Olbert, Dossenheim (DE); Ulrike Wegerle, Worms (DE); Grigorios Kolios, Neustadt (DE); Albena Kostova, Mannheim (DE)

(73) Assignee: BASF SE (DE)

( * ) Notice: Subject to any disclaimer, the term of this patent is extended or adjusted under 35 U.S.C. 154(b) by 405 days.

(21) Appl. No.: 13/564,090

(22) Filed: Aug. 1, 2012

(65) Prior Publication Data

US 2013/0035529 A1     Feb. 7, 2013

Related U.S. Application Data

(60) Provisional application No. 61/514,086, filed on Aug. 2, 2011.

(51) Int. Cl.
| | |
|---|---|
| *C07C 5/48* | (2006.01) |
| *C07C 5/42* | (2006.01) |
| *B01J 8/00* | (2006.01) |
| *B01J 8/02* | (2006.01) |
| *B01J 19/00* | (2006.01) |
| *B01J 19/24* | (2006.01) |

(52) U.S. Cl.
CPC ....................................... *C07C 5/48* (2013.01)

(58) Field of Classification Search
CPC .......... B01J 7/00; B01J 19/00; B01J 19/0013; B01J 19/0053; B01J 19/24; B01J 19/2485; B01J 8/00; B01J 8/008; B01J 8/0285; B01J 2219/00; B01J 2219/00006; B01J 2219/0004; B01J 2219/00094; B01J 2219/00835; B01J 2219/00873; B01J 2219/2479; B01J 16/00; B01J 16/005; C07C 5/00; C07C 5/32; C07C 5/321; C07C 5/42; C07C 5/48; C07C 11/00; C07C 11/02; C07C 11/06; C07C 11/08; C07C 11/09; C07C 11/10; C07C 11/107; C07C 11/12; C07C 11/14; C07C 11/16
USPC ................. 422/129, 198, 600, 630, 631, 633; 585/350, 379, 380
See application file for complete search history.

(56) References Cited

U.S. PATENT DOCUMENTS

| | | | | |
|---|---|---|---|---|
| 5,023,276 | A | * | 6/1991 | Yarrington et al. ........... 518/703 |
| 5,678,725 | A | * | 10/1997 | Yamada et al. .......... 220/592.21 |
| 7,034,195 | B2 | | 4/2006 | Schindler et al. |

(Continued)

FOREIGN PATENT DOCUMENTS

DE           40 26 566 A1     2/1992

OTHER PUBLICATIONS

U.S. Appl. No. 13/564,028, filed Aug. 1, 2012, Olbert et al.

*Primary Examiner* — Natasha Young
(74) *Attorney, Agent, or Firm* — Drinker Biddle & Reath LLP

(57) ABSTRACT

The invention relates to a process for the autothermal gas-phase dehydrogenation of a hydrocarbon-comprising gas stream by means of an oxygen-comprising gas stream over a heterogeneous catalyst configured as a monolith to give a reaction gas mixture and regeneration of the catalyst in a reactor in the form of a cylinder or prism, wherein the reactor is operated alternately in the production mode of the autothermal gas-phase dehydrogenation and in the regeneration mode.

19 Claims, 3 Drawing Sheets

(56) References Cited

U.S. PATENT DOCUMENTS

Figure 1A:
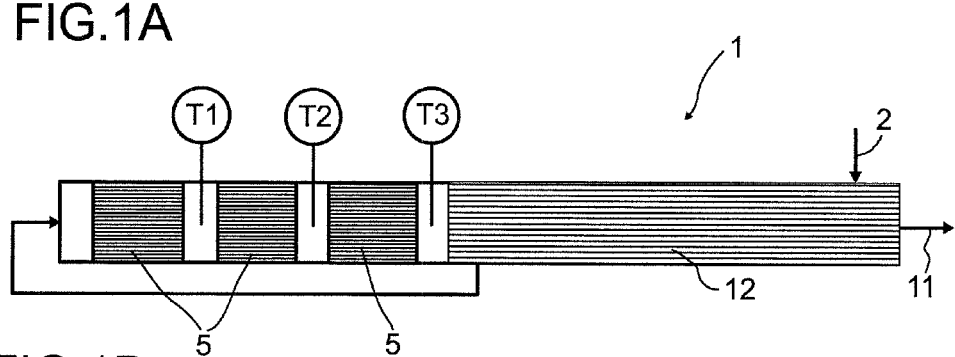

| | | | |
|---|---|---|---|
| 7,255,848 B2 * | 8/2007 | Deluga et al. | 423/648.1 |
| 7,270,688 B2 * | 9/2007 | Childress et al. | 48/61 |
| 7,388,109 B2 * | 6/2008 | Machhammer et al. | 562/549 |
| 2007/0175094 A1 * | 8/2007 | Reinke et al. | 48/127.9 |
| 2008/0119673 A1 | 5/2008 | Hechler et al. | |

* cited by examiner

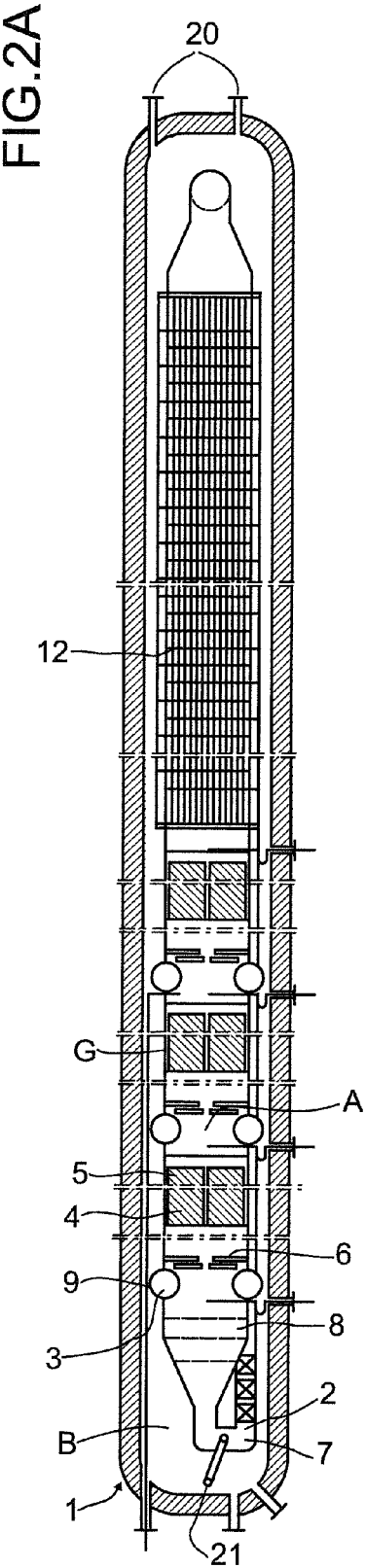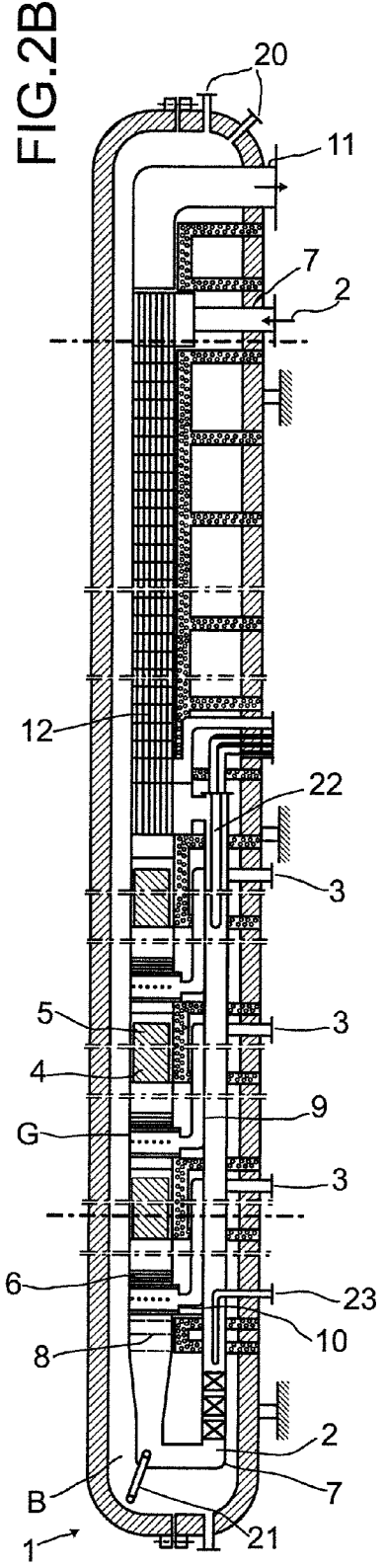

CONTINUOUS PROCESS FOR CARRYING OUT AUTOTHERMAL GAS-PHASE DEHYDROGENATIONS

CROSS-REFERENCE TO RELATED APPLICATIONS

This application claims benefit (under 35 USC 119(e)) of U.S. Provisional Application 61/514,086, filed Aug. 2, 2011, which is incorporated by reference.

BACKGROUND OF THE INVENTION

The invention relates to a continuous process for the autothermal gas-phase dehydrogenation of a hydrocarbon-comprising gas stream and regeneration of the catalyst which is configured as a monolith, and a use of the process.

Ceramic or metallic monoliths have become established as catalyst supports for noble metal catalysts in mobile and stationary offgas purification. The channels offer a low flow resistance to the gas stream while at the same time allowing uniform accessibility to the outer catalyst surface for gaseous reaction media. This is advantageous compared to irregular beds in which numerous diversions in the flow around the particles result in a large pressure drop and the catalyst surface may not be uniformly utilized. The use of monoliths is of general interest for catalytic processes which have high volume flows and in which the reaction is carried out adiabatically at high temperatures. In chemical production engineering, these features apply particularly to dehydrogenation reactions which proceed in a temperature range from 400° C. to 700° C.

Advances in catalyst technology make it possible to carry out the selective combustion of the dehydrogenation hydrogen in the presence of hydrocarbons, as described, for example, in U.S. Pat. No. 7,034,195. Such a mode of operation is referred to as autothermal dehydrogenation and allows dehydrogenation reactors to be heated directly, so that complicated apparatuses for indirect preheating and intermediate heating of the reaction mixture are dispensed with. Such a process is, for example, described in US 2008/0119673. However, this process has the serious disadvantage that the dehydrogenation is carried out over a heterogeneous catalyst in pellet form: the high flow resistance of pellet beds requires a large reactor cross section and a correspondingly low flow velocity in order to limit the pressure drop in the catalytically active bed. This disadvantage is compensated by means of a very complicated apparatus for introducing and distributing the oxygen, which partly negates the advantage of autothermal dehydrogenation.

The European patent application EP 09 177 649.2, which is not a prior publication, discloses a reactor and a process for the autothermal gas-phase dehydrogenation of hydrocarbons using heterogeneous catalysts configured as monoliths, which ensures control of the combustible reaction media at the high reaction temperatures, frequently in the range from about 400 to 700° C., and allows simple accessibility and handling of the monoliths, in particular when equipping the reactor or in the case of catalyst replacement.

EP 09 177 649.2 provides a reactor in the form of an essentially horizontal cylinder for carrying out an autothermal gas-phase dehydrogenation of a hydrocarbon-comprising gas stream by means of an oxygen-comprising gas stream over a heterogeneous catalyst configured as a monolith to give a reaction gas mixture, where the interior space of the reactor is divided by means of a detachable cylindrical or prismatic housing G which is arranged in the longitudinal direction of the reactor and is gastight in the circumferential direction and is open at both end faces into an inner region A which has one or more catalytically active zones and in which a packing composed of monoliths stacked on top of one another, next to one another and behind one another is provided in each catalytically active zone and a mixing zone having fixed internals is provided before each catalytically active zone and an outer region B arranged coaxially with the inner region A, with one or more feed lines for the hydrocarbon-comprising gas stream to be dehydrogenated into the outer region B, diversion of the hydrocarbon stream to be dehydrogenated at one end of the reactor and introduction via a flow equalizer into the inner region A, with one or more, independently regulable feed lines, with each feed line supplying one or more distributor chambers, for the oxygen-comprising gas stream into each of the mixing zones and with a discharge line for the reaction mixture of the autothermal gas-phase dehydrogenation at the same end of the reactor as the feed line for the hydrocarbon stream to be dehydrogenated.

At the end of the reactor at which the discharge line for the reaction gas mixture of the autothermal gas-phase dehydrogenation is arranged, it is advantageous to provide a shell-and-tube heat exchanger having a bundle of tubes through which the reaction gas mixture of the autothermal gas-phase dehydrogenation is passed and intermediate spaces between the tubes through which the hydrocarbon-comprising gas stream to be dehydrogenated is passed in countercurrent to the reaction gas mixture of the autothermal gas-phase dehydrogenation.

However, EP 10 196 216.5 describes an improved reactor for autothermal gas-phase dehydrogenation, which has safety advantages and also solves the problems of sealing the shell-and-tube heat exchanger.

The known reactors for autothermal gas-phase dehydrogenation are operated with two reactors of the same type being provided and a first reactor being operated in the functional mode of the autothermal gas-phase dehydrogenation until the activity of the catalyst decreases to such an extent that it has to be regenerated, whereupon the reactor is switched over to the regeneration mode and a second reactor of the same type is switched to the production mode of the autothermal gas-phase dehydrogenation.

Plants for autothermal gas-phase dehydrogenation generally produce very large product streams, frequently of an order of magnitude of from 150 000 to 200 000 metric tons per annum, which after the dehydrogenation are passed to further process steps, i.e., in particular, work-up and/or reaction steps. These process steps have to operate continuously since in the case of the large mass flows a fresh start or a change in load would be too complicated.

In addition, in the case of the mode of operation according to the prior art using two reactors which are operated alternately in the production mode and the regeneration mode, the outlay in terms of capital costs, safety, working time, etc., for switching over between the two modes of operation is high in industrial plants. A scale-up is complicated because two reactors have to be made appropriately larger to achieve an increase in capacity. Furthermore, a buffer vessel is generally necessary in the mode of operation according to the prior art using two reactors operated alternately in the production mode and the regeneration mode in order to compensate for the switch-over time.

A SUMMARY OF THE INVENTION

It was therefore an object of the invention to provide a continuous process for autothermal gas-phase dehydrogenation which does not have the above disadvantages.

The object is achieved by a continuous process for the autothermal gas-phase dehydrogenation of a hydrocarbon-comprising gas stream by means of an oxygen-comprising gas stream over a heterogeneous catalyst configured as a monolith to give a reaction gas mixture and regeneration of the catalyst in a reactor in the form of a cylinder or prism, where the interior space of the reactor is divided by means of a cylindrical or prismatic gastight housing G arranged in the longitudinal direction of the reactor into an inner region A which has one or more catalytically active zones and in which a packing composed of monoliths stacked on top of one another, next to one another and behind one another is provided in each catalytically active zone and a mixing zone having fixed internals is provided before each catalytically active zone and an outer region B arranged coaxially with the inner region A, and a heat exchanger is provided at one end of the reactor next to the housing G, with one or more feed lines for the hydrocarbon-comprising gas stream to be dehydrogenated, with one or more feed lines, where each feed line supplies one or more distributor chambers, for the oxygen-comprising gas stream into each of the mixing zones and with a discharge line for the reaction gas mixture of the autothermal gas-phase dehydrogenation, where the outer region B is supplied with a gas which is inert under the reaction conditions of the autothermal gas-phase dehydrogenation and the hydrocarbon-comprising gas stream to be dehydrogenated is introduced via a feed line into the heat exchanger, heated in the heat exchanger by indirect heat exchange in countercurrent with the reaction gas mixture and conveyed further to the end of the reactor opposite the heat exchanger, diverted there, introduced via a flow equalizer into the inner region A and mixed in the mixing zones with the oxygen-comprising gas stream, whereupon the autothermal gas-phase dehydrogenation takes place in the inner region A of the reactor, wherein the reactor is operated alternately in the production mode of the autothermal gas-phase dehydrogenation and in the regeneration mode, where the production mode of the autothermal gas-phase dehydrogenation is operated until the increase in temperature of the reaction gas mixture after exit from the last catalytically active zone and before entry into the heat exchanger, based on the point in time after which the conversion does not fluctuate by more than 1%, based on the final conversion, does not exceed 5 K, whereupon the reactor is switched over to the regeneration mode with introduction of an inert regeneration gas which comprises at least 10% by weight of oxygen, based on the total weight of the regeneration gas.

A BRIEF DESCRIPTION OF THE FIGURES

Figure 1B:
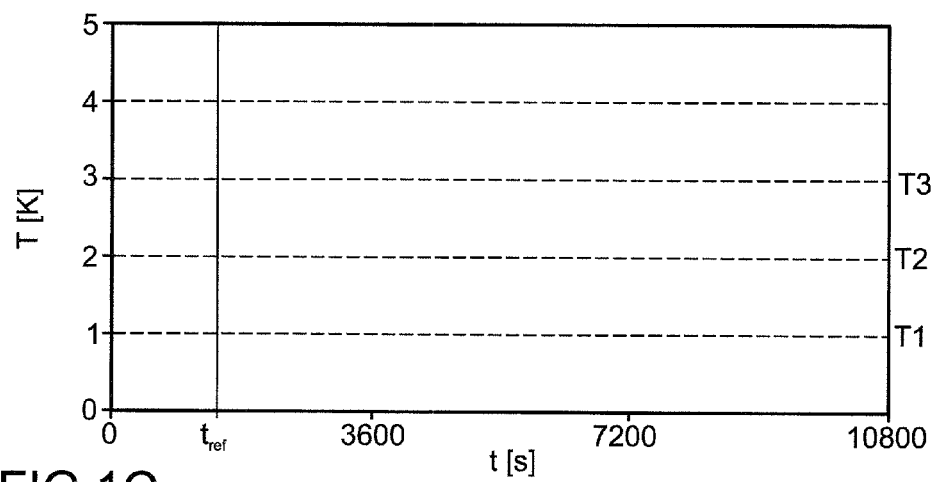
Figure 1C:
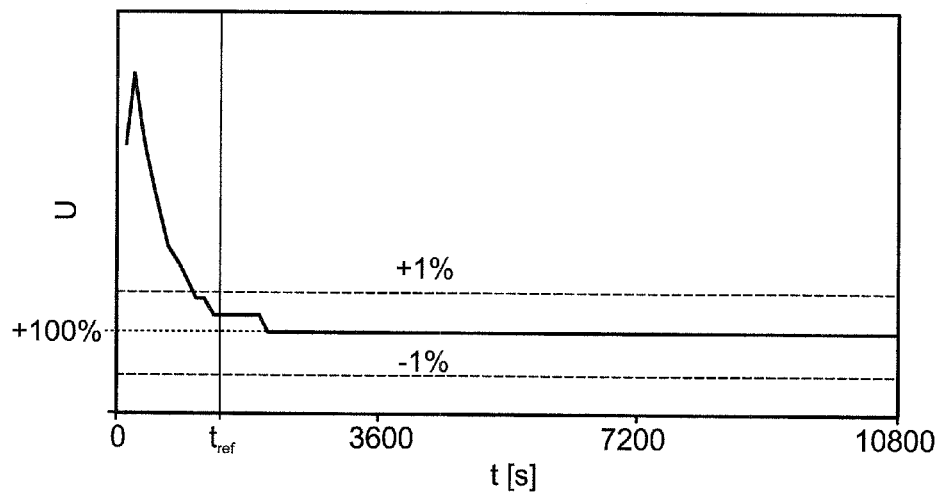
Figure 3:
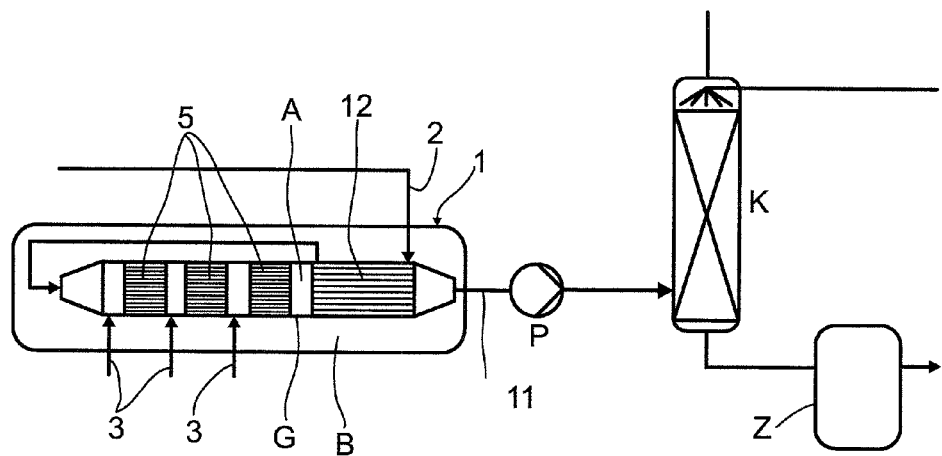
Figure 4:
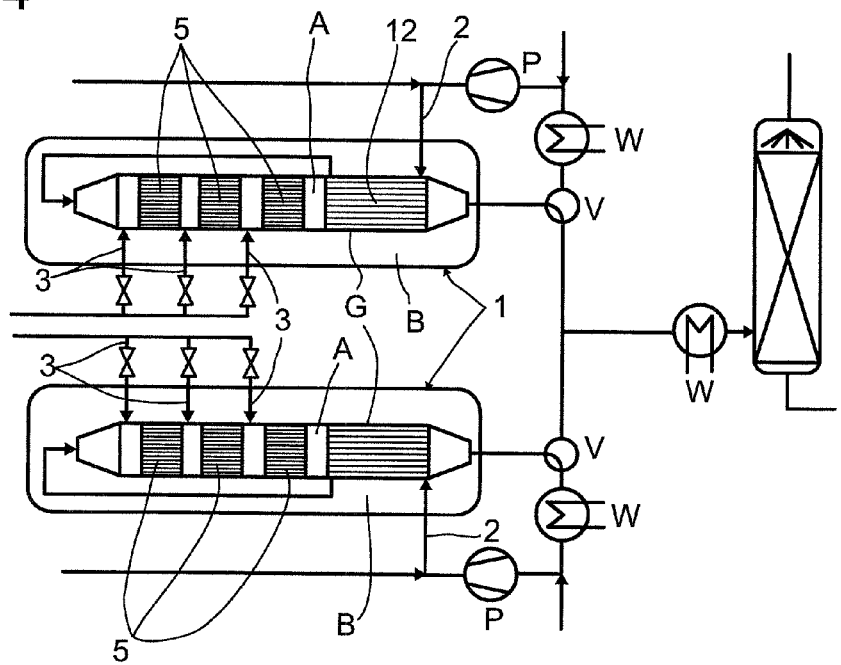

FIG. 1A schematically shows the preferred embodiment of a reactor 1 according to the invention having, by way of example, three catalytically active zones 5 arranged after one another and a heat exchanger 12, where T1 to T3 denotes the temperatures at the exit from the first, second and third, respectively, catalytically active zone 5, FIG. 1B schematically shows the change in the temperature T, in kelvin, of the reaction gas mixture on exiting from the last catalytically active zone and before entry into the heat exchanger, as a function of time in seconds, FIG. 1C schematically shows the change in the conversion in percent, as a function of time in seconds, FIG. 2A shows a longitudinal section through a preferred embodiment of a reactor according to the invention in the horizontal plane, FIG. 2B shows a longitudinal section through the same reactor in a vertical plane, FIG. 3 schematically shows a preferred embodiment of a plant for carrying out an autothermal gas-phase dehydrogenation by the process of the invention and FIG. 4 schematically shows a plant for carrying out an autothermal gas-phase dehydrogenation according to the prior art.

A DETAILED DESCRIPTION OF THE INVENTION

With increasing operating time of the autothermal gas-phase dehydrogenation the activity of the dehydrogenation catalyst decreases with the consequence that the reaction gas mixture becomes hotter at the exit from the reactor.

The invention utilizes this increase in temperature of the reaction gas mixture at the exit from the last catalytically active zone and before entry into the heat exchanger as signal for switching over from the production mode to the regeneration mode: for this purpose, the temperature of the reaction gas mixture is measured continuously in a manner known to those skilled in the art, e.g. by means of a thermocouple, and compared with the measured value for the temperature at time zero. Here, time zero is determined as follows: at the beginning of the production mode, the temperature initially fluctuates, as usual, during a start-up phase until a pseudo-steady-state is established after which the temperature gradient with respect to time then increases linearly in the range from about 0 to 2 kelvin per hour. This point in time after which the pseudo-steady-state operating state with a largely linear increase in the temperature gradient over time is established corresponds to the point in time after which the conversion of the autothermal gas-phase dehydrogenation is virtually constant, i.e. in the present case fluctuates, in particular, by not more than 1%, based on the final conversion. This point in time after which the conversion of the autothermal gas-phase dehydrogenation does not fluctuate by more than 1%, based on the final conversion, is for the present purposes taken as time zero for the measurement of the increase in temperature of the reaction gas mixture at the exit from the last catalytically active zone.

In a preferred embodiment, time zero for the measurement of the increase in temperature of the reaction gas mixture on exiting the last catalytically active zone and before entry into the heat exchanger is taken as the points in time at which the conversion does not fluctuate by more than 0.5%, based on the final conversion.

Furthermore, the time zero for the measurement of the increase in temperature of the reaction gas mixture on exiting the last catalytically active zone and before entry into the heat exchanger is taken as the point in time at which the conversion does not fluctuate by more than 0.2%, based on the final conversion.

How the conversion of an autothermal gas-phase dehydrogenation can be determined continuously is generally known to those skilled in the art. In chemical reaction technology, the conversion is, as is known, the proportion of a starting material which has been converted into other chemical materials by chemical reaction on leaving the reactor (cf. Wikipedia). This proportion can be determined continuously in a manner known to those skilled in the art using known analytical methods, in particular by means of on-line gas chromatography (GC) or Fourier transform infrared spectroscopy (FTIR). The response time of GC is known to be in the region of 20 minutes or in the region of about 1 minute in the case of micro-GC. FTIR has a response time in the region of 30 seconds.

In a preferred embodiment, the relatively complicated on-line analysis for determining the conversion can be replaced by a simple temperature measurement:

It has been found that the time zero for the measurement of the increase in temperature of the reaction gas mixture, i.e. the point in time after which the conversion of the autothermal gas-phase dehydrogenation does not fluctuate by more than 1%, based on the final conversion, corresponds, when a single catalytically active zone is used in the inner region A, to the point in time after which the temperature of the reaction gas mixture increases linearly over a period of at least 15 minutes. Time zero can thus be determined by means of a simple measurement of the temperature of the reaction gas mixture. In the preferred embodiment, the more complicated on-line analysis for determining the conversion can therefore be dispensed with; in addition, the dynamics of the temperature measurement are faster than the dynamics of concentration measurements.

In the case of the embodiment in which two or more catalytically active zones arranged after one another are provided, time zero for the measurement of the increase in temperature of the reaction gas mixture on exiting from the last catalytically active zone is preferably determined as the point in time after which the temperature at the exit from each catalytically active zone in each case increases to a greater extent than the temperature at the exit from the immediately preceding catalytically active zone.

The production mode is operated as long as the increase in temperature of the reaction gas mixture on exiting the last catalytically active zone and before entry into the heat exchanger compared to the above-defined starting time (time zero) does not exceed the value of 5 K indicated above. This means that the switch-over from the production mode to the regeneration mode can be carried out any point in time as long as the increase in temperature of the reaction gas mixture does not exceed, in the above-defined manner, the above-defined value. For economic reasons, preference is given to exploiting the maximum duration for the production mode, i.e. to operate very close to the upper limit for the increase in temperature.

In an advantageous embodiment, the production mode is ended and the reactor is switched over to the regeneration mode as soon as the increase in temperature of the reaction gas mixture on exiting the last catalytically active mode and before entry into the heat exchanger at the above-defined starting time exceeds 4 K.

It is also advantageous to end the production mode and switch the reactor over to the regeneration mode as soon as the increase in temperature of the reaction gas mixture on exit from the discharge line exceeds 3 K at the above-defined starting time.

As stated above, the starting time (time zero) is taken as the point in time after which the conversion of the autothermal gas-phase dehydrogenation does not fluctuate by more than 1%, based on the final conversion, preferably the point in time at which the conversion does not fluctuate by more than 0.5%, based on the final conversion, more preferably the point in time at which the conversion does not fluctuate by more than 0.2%, based on the final conversion.

In the process of the invention, the operating time in the production mode is limited as defined above; subsequently, operation is switched over to the regeneration mode using a regeneration gas which comprises a high proportion of at least 10% by weight of oxygen, based on the total weight, and makes it possible to make the reactor available for the production mode again within a relatively short regeneration time.

The mode of operation according to the invention makes it possible for not more than 15% of the total operating time to be taken up by the regeneration mode in each operating cycle comprising in each case one production mode and one regeneration mode.

The operating time for a production mode is typically 3 hours or longer.

Preference is given to not more than 10%, more preferably not more than 5%, of the total operating time being taken up by the regeneration mode in each operating cycle comprising in each case one production mode and one regeneration mode.

The process of the invention is carried out in a reactor as is known from EP 10 196 216.5. This is a reactor in the form of a cylinder or prism, where
 the interior space of the reactor is divided by means of a cylindrical or prismatic gastight housing G arranged in the longitudinal direction of the reactor into
   an inner region A which has one or more catalytically active zones and in which a packing composed of monoliths stacked on top of one another, next to one another and behind one another is provided in each catalytically active zone and a mixing zone having fixed internals is provided before each catalytically active zone and
   an outer region B arranged coaxially with the inner region A, and
 a heat exchanger is provided at one end of the reactor next to the housing G,
 with one or more feed lines for the hydrocarbon-comprising gas stream to be dehydrogenated,
 with one or more, independently regulable feed lines, where each feed line supplies one or more distributor chambers, for the oxygen-comprising gas stream in each of the mixing zones and
 with a discharge line for the reaction gas mixture of the autothermal gas-phase dehydrogenation, where
 the outer region B is supplied with a gas which is inert under the reaction conditions of the autothermal gas-phase dehydrogenation and
 the hydrocarbon-comprising gas stream to be dehydrogenated is introduced via a feed line into the heat exchanger, heated in the heat exchanger by indirect heat exchange in countercurrent with the reaction gas mixture and conveyed further to the end of the reactor opposite the heat exchanger, diverted there, introduced via a flow equalizer into the inner region A and mixed in the mixing zones with the oxygen-comprising gas stream, whereupon the autothermal gas-phase dehydrogenation takes place in the inner region A of the reactor.

The reactor is preferably configured as an essentially horizontal cylinder or prism.

The reactor is equipped with an outer reactor wall, i.e. a pressure-bearing shell, which is not touched by a medium, neither by the hydrocarbon-comprising stream nor by the oxygen-comprising stream.

In the longitudinal direction of the reactor there is a cylindrical or prismatic housing G which divides the interior space of the reactor into an inner region A and an outer region B arranged concentrically around the inner region A.

The outer region B is supplied with a gas which is inert under the reaction conditions of the autothermal gas-phase dehydrogenation, i.e. a gas or gas mixture which does not participate directly in the reaction of the autothermal gas-phase dehydrogenation, in particular a gas selected from among water, carbon dioxide, nitrogen and noble gases or mixtures thereof. Preference is given to using steam as gas which is inert under the reaction conditions of the autothermal gas-phase dehydrogenation since this can easily be separated off again from the reaction gas mixture by condensation.

The gas which is inert under the reaction conditions of the autothermal gas-phase dehydrogenation is preferably passed through the inner region A as purge gas stream having a low mass flow compared to the mass flow of the hydrocarbon-comprising gas stream, i.e. a mass flow of from $1/5$ to $1/100$, preferably a mass flow of from $1/10$ to $1/50$, based on the mass flow of the hydrocarbon-comprising gas stream, under a low gauge pressure of from 2 to 50 mbar, preferably from 25 to 30 mbar, based on the pressure in the inner region A.

The purge gas stream can advantageously be passed through the outer region B by being introduced into the outer region B of the reactor via one or more feed lines at one end of the reactor and being passed on into the inner region A of the reactor at the opposite end of the reactor, preferably via one or more connecting line(s) advantageously arranged at an angle other than 90° to the feed line for the hydrocarbon-comprising gas stream to be dehydrogenated.

The one or more connecting line(s) which carry the purge gas stream from the outer region B into the inner region A are preferably configured so as to be free of reverse flow, for example by having a helical shape. The inlet from the outer region B into the connecting line for the purge gas stream should preferably be arranged at a point which is as high as possible in the outer region B of the reactor.

The purge gas stream continually flushes the outer region B of the reactor and keeps this free of components of the reaction gas mixture.

A heat exchanger, which can be, in particular, a shell-and-tube heat exchanger or a plate heat exchanger, is connected at one end of the housing G. In the case of a shell-and-tube heat exchanger, the connection between this and the housing G is configured so that the inner region A communicates with the interior space of the tubes of the shell-and-tube heat exchanger. In the case of a plate heat exchanger, the inner region A of the reactor communicates with the gaps between the plates of the plate heat exchanger.

The intermediate space between the tubes of the shell-and-tube heat exchanger or between two plates welded together to form a heat exchange plate of the plate heat exchanger is connected via a line which leads to the end of the reactor opposite the heat exchanger and is diverted there to the end of the housing G opposite the heat exchanger and thus the inner region of the reactor in such a way that it is sealed in a gastight manner from the outer region B.

The hydrocarbon-comprising stream is passed through the intermediate space between the tubes of the shell-and-tube heat exchanger or in the case of a plate heat exchanger through the intermediate spaces between the plates forming a heat exchange plate, heated by the process gas stream circulating in countercurrent through the tubes or through the gap between the plates of the plate heat exchanger, conducted to the opposite end of the reactor, diverted there and introduced into the inner region A of the housing.

The autothermal gas-phase dehydrogenation takes place over a heterogeneous catalyst which is present in the form of monoliths.

The monoliths which are stacked next to one another, above one another and after one another to form a packing are preferably enveloped in an expanded mat or in a mineral fiber nonwoven and placed in a casing having a clamping device. As mineral fiber nonwovens, preference is given to nonwovens as are known for use for offgas catalysts, for example Interam® mounting mats from 3M®.

The monoliths enveloped in expanded mats are arranged in a housing which is installed, preferably in a thermally insulated manner, more preferably loose, in the reactor and is preferably configured as a cuboid.

The sidewalls of the housing configured as a cuboid can preferably be taken off individually so that a complete packing or individual monoliths of a packing in a catalytically active zone can be replaced.

The individual monoliths are stacked next to one another, above one another and after one another, in the required number, in order to fill out a catalytically active zone to form a packing.

A mixing zone having fixed internals which are not catalytically active is provided before each packing. Mixing of the hydrocarbon-comprising gas stream with the oxygen-comprising stream occurs in the mixing zone, with the mixing of the oxygen-comprising gas stream with the hydrocarbon-comprising feed stream occurring in the first mixing zone in the flow direction and intermediate introduction of an oxygen-comprising gas stream into the hydrocarbon-comprising reaction mixture still to be dehydrogenated being carried out in each of the subsequent mixing zones in the flow direction.

The oxygen-comprising gas stream is fed via one or more feed lines into each of the mixing zones, with each feed line supplying one or more distributor chambers. In the embodiment having a plurality of feed lines, these can preferably be regulated independently of one another.

The hydrocarbon-comprising gas stream to be dehydrogenated can preferably be introduced into the heat exchanger at two or more places, in particular as a main stream having a higher mass flow and one or more secondary streams having a lower mass flow compared to the main stream.

To heat the hydrocarbon-comprising gas stream to be dehydrogenated, it is possible to provide one or more additional heating means in addition to the heat exchanger. As additional heating means, the introduction of hydrogen through the feed line for the hydrocarbon-comprising gas stream to be dehydrogenated can be provided, as close as possible to the entry into the mixing zones arranged before each catalytically active zone.

As an alternative, heating of the oxygen-comprising gas stream can also be effected by introducing fuel, for example hydrogen or butane, into one or all of the feed lines for the oxygen-comprising gas stream, in which case the concentration of the fuel in the oxygen-comprising gas stream has to be restricted so as to be far below the lower explosion limit. The concentrations of the fuel in the feed lines for the oxygen-comprising gas stream should advantageously be able to be set individually.

The invention also provides a plant for carrying out an autothermal gas-phase dehydrogenation using a reactor as described above, wherein a reservoir is provided for the reaction gas mixture leaving the reactor via the discharge line, preferably after condensation of the reaction gas mixture, before the reaction gas mixture is passed onto a work-up plant.

The buffer vessel which is also required according to the prior art in the case of alternating production mode/regeneration mode is advantageously made twice or three times as large as in the prior art in order to compensate for the short downtime during the regeneration phase. In this way, the work-up after the dehydrogenation can continue to operate continuously, as required.

The invention also provides for the use of the above-described reactor or a plant as described above in a process for carrying out an autothermal gas-phase dehydrogenation.

The autothermal gas-phase dehydrogenation is preferably a dehydrogenation of propane, of butane, of isobutane, of butene or of ethylbenzene.

The process of the invention thus makes it possible to carry out an autothermal gas-phase dehydrogenation continuously in a single reactor and accordingly using a single catalyst charge without the plant having to be shut down for the purpose of regenerating the catalyst. This corresponds to an availability, calculated for the single reactor, of 95% compared to 50% according to the prior art. In the alternate operation of two reactors of the same type, the switching-over problems accordingly do not occur and the periphery is correspondingly significantly simpler. In addition, scale-up is significantly cheaper since, in contrast to the prior art, it is not necessary to make two reactors larger at the same time. In addition, the operating life of the dehydrogenation catalyst is also increased: owing to the limitation according to the invention of the operating time for the production mode, deep-seated deposits on the catalyst can be avoided, as a result of which the regenerability of the catalyst is improved.

The invention is illustrated below in with the aid of an example and drawings.

Example

A dehydrogenation of butane was carried out firstly in a plant according to the prior art, as is shown schematically in FIG. 4 (comparative example), and secondly in a plant having a single reactor as is shown schematically in FIG. 3 (example according to the invention).

The reactor was supplied with 672.87 kg/h of a hydrocarbon-comprising gas stream having a temperature of 200° C. and a pressure of 2 bar absolute and the following composition:

|  | kg/h |
|---|---|
| $C_4H_{10}$ | 507.3211 |
| $C_4H_8$ | 21.4382 |
| $C_4H_6$ | 1.3058 |
| $H_2O$ | 133.3412 |
| $CH_4$ | 4.1280 |
| $CO_x$ | 0.0000 |
| $O_2$ | 0.0000 |
| $H_2$ | 5.3395 |
| $N_2$ | 0.0000 |

Furthermore, an oxygen-comprising gas stream 3 having a temperature of 240° C. and a pressure of 2 bar absolute was fed into the reactor via three independently regulable lines 9 with a gas stream of 20.32 kg/h of oxygen and 69.44 kg/h of steam being fed in via the first, viewed in the flow direction, feed line, a gas stream of 11.45 kg/h of oxygen and 39.12 kg/h of steam being fed in via the feed line 9 arranged at a second, viewed in the flow direction, place on the reactor and a gas stream 3 comprising 8.57 kg/h of oxygen and 29.29 kg/h of steam being fed in via a feed line 9 arranged at a third, viewed in the flow direction, place.

Comparative Example

When the autothermal gas-phase dehydrogenation was carried out under the above operating conditions in a plant corresponding to FIG. 4 over a total operating time of 12 hours, the first reactor was operated in the production mode and the second reactor was operated in the regeneration mode. The conversion at the starting time was 40.5% and that at the end of the operating time of 12 hours was only 39.65%, i.e. an average over time of 40.00%.

Example According to the Invention

A plant corresponding to the schematic depiction in FIG. 3, i.e. with a single reactor, was operated under the same operating conditions. The operating time for the production mode was 3 hours, and the operating time for the regeneration mode was 10 minutes, i.e. only about 5% of the total time of an operating cycle. The conversion was about 40.5% during the entire operating time for the production mode.

In the drawing:

FIG. 1A schematically shows the preferred embodiment of a reactor 1 according to the invention having, by way of example, three catalytically active zones 5 arranged after one another and a heat exchanger 12, where T1 to T3 denotes the temperatures at the exit from the first, second and third, respectively, catalytically active zone 5, FIG. 1B schematically shows the change in the temperature T, in kelvin, of the reaction gas mixture on exiting from the last catalytically active zone and before entry into the heat exchanger, as a function of time in seconds, FIG. 1C schematically shows the change in the conversion in percent, as a function of time in seconds, FIG. 2A shows a longitudinal section through a preferred embodiment of a reactor according to the invention in the horizontal plane, FIG. 2B shows a longitudinal section through the same reactor in a vertical plane, FIG. 3 schematically shows a preferred embodiment of a plant for carrying out an autothermal gas-phase dehydrogenation by the process of the invention and FIG. 4 schematically shows a plant for carrying out an autothermal gas-phase dehydrogenation according to the prior art.

In the figures, identical reference symbols in each case denote identical or corresponding features.

The schematic depiction of a preferred reactor according to the invention having three catalytically active zones 5 arranged after one another indicates the places in the reactor at which the temperatures T1 to T3 are measured, i.e. temperature T1 at the exit from the first catalytically active zone 5 through which the reaction mixture flows, the temperature T2 on exit from the second, viewed in the flow direction, catalytically active zone through which the reaction gas mixture flows and the temperature T3 at the exit from the third and last, viewed in the flow direction, catalytically active zone 5 and before the entry into the heat exchanger 12.

FIG. 1B shows the above temperatures T1 to T3 as a function of time in a graph which shows the time t in seconds on the abscissa and the temperature T in kelvin on the ordinate.

The figure shows that the temperature of the reaction gas mixture on exiting from the discharge line initially fluctuates in the start-up phase of the production mode until a steady state after which the increase in temperature is largely linear is established. The point in time after which the steady state is established is taken as time zero ($t_{ref}$) (starting point) for the determination of the increase in temperature, after which the production mode is stopped and the reactor is switched to the regeneration mode.

FIG. 1B shows that the point in time after which the temperature T2 increases more steeply than the temperature T1 and the temperature T3 likewise increases more steeply than the temperature T2 is taken as time zero ($t_{ref}$).

FIG. 1C shows corresponding changes in the standardized conversion U in percent as a function of time in seconds: time zero ($t_{ref}$) corresponds to the point in time after which the conversion, as is shown schematically in FIG. 1C, goes over into a steady state, i.e. does not fluctuate by more than 1%, based on the final conversion, preferably by not more than 0.5%, based on the final conversion, more preferably by not more than 0.2%, based on the final conversion.

The longitudinal section in the horizontal plane in FIG. 2A schematically shows a preferred embodiment of a reactor for carrying out the process of the invention. The housing G divides the inner space of the reactor into an inner region A and an outer region B. The reactor is supplied with the hydrocarbon-comprising gas stream 2 to be dehydrogenated via a feed line 7 and with an oxygen-comprising gas stream 3 via three feed lines 9. In the inner region A of the reactor, there are, by way of example, three catalytically active zones 5 formed by monoliths 4. A zone 6 having fixed internals is arranged in each catalytically active zone. The hydrogen-comprising gas stream 2 is heated by indirect heat exchange with the reaction gas mixture in a heat exchanger 12, introduced into the other end of the reactor, diverted there and introduced via a flow equalizer 8 into the inner region A in which the autothermal gas-phase dehydrogenation takes place in the catalytically active zones 5. The preferred embodiment shown in FIG. 2A shows feed lines 20 for a purge gas stream on the right-hand side of the figure and a connecting line 21 for the purge gas stream from the outer region B of the reactor and the feed line 7 for the hydrocarbon-comprising gas stream 2 to be dehydrogenated on the left-hand side of the figure.

The longitudinal section in a vertical plane in FIG. 2B additionally shows preferred facilities, namely additional heating means, which can advantageously be used: an electric heating means 22 and a feed line 23 for hydrogen as fuel gas into the feed line 7 for the hydrocarbon-comprising gas stream 2 to be dehydrogenated.

FIG. 3 schematically shows a preferred plant for carrying out the process of the invention in a single reactor 1 having a housing G which divides the interior space of the reactor into an inner region A and an outer region B, with, by way of example, three catalytically active zones 5 made up of monoliths which are not shown in detail and also a heat exchanger 12 being arranged in the inner region A. A hydrocarbon-comprising gas stream 2 and an oxygen-comprising gas stream 3 in three substreams are fed to the reactor 1. The reaction gas mixture is taken off from the reactor via the discharge line 11, fed via a pump P and heat exchanger W to a scrubbing column K and further to an intermediate buffer Z before being passed onto, in particular, work-up by distillation.

The schematic depiction in FIG. 4 shows, in contrast, a plant according to the prior art having two reactors 1 of the same type.

The invention claimed is:

1. A process for the autothermal gas-phase dehydrogenation of a hydrocarbon-comprising gas stream by means of an oxygen-comprising gas stream over a heterogeneous catalyst configured as a monolith to give a reaction gas mixture and regenerating the catalyst in a reactor in the form of a cylinder or prism, wherein
   the interior space of the reactor is divided by means of a cylindrical or prismatic gastight housing G arranged in the longitudinal direction of the reactor into
   an inner region A which has one or more catalytically active zones arranged after one another and in which a packing composed of monoliths stacked on top of one another, next to one another and after one another is provided in each catalytically active zone and a mixing zone having fixed internals is provided before each catalytically active zone and
   an outer region B arranged coaxially with the inner region A, and
   a heat exchanger is provided at one end of the reactor next to the housing G,
   with one or more feed lines for the hydrocarbon-comprising gas stream to be dehydrogenated,
   with one or more feed lines for the oxygen-comprising gas stream in each of the mixing zones, where each feed line supplies one or more distributor chambers, and
   with a discharge line for the reaction gas mixture of the autothermal gas-phase dehydrogenation, where
   the outer region B is supplied with a gas which is inert under the reaction conditions of the autothermal gas-phase dehydrogenation and
   the hydrocarbon-comprising gas stream to be dehydrogenated is introduced via a feed line into the heat exchanger, heated in the heat exchanger by indirect heat exchange in countercurrent with the reaction gas mixture and conveyed further to the end of the reactor opposite the heat exchanger, diverted there, introduced via a flow equalizer into the inner region A and mixed in the mixing zones with the oxygen-comprising gas stream, whereupon the autothermal gas-phase dehydrogenation takes place in the inner region A of the reactor, wherein
   the reactor is operated alternately in the production mode of the autothermal gas-phase dehydrogenation and in the regeneration mode, where
   the production mode of the autothermal gas-phase dehydrogenation is operated until the increase in temperature of the reaction gas mixture after exit from the last catalytically active zone viewed in the flow direction and before entry into the heat exchanger, based on the point in time after which the conversion does not fluctuate by more than 1%, based on the final conversion, does not exceed 5 K, whereupon
   the reactor is switched over to the regeneration mode with introduction of an inert regeneration gas which comprises at least 10% by weight of oxygen, based on the total weight of the regeneration gas.

2. The process according to claim 1, wherein the point in time after which the conversion does not fluctuate by more than 1%, based on the final conversion, is determined as the point in time after which the increase in temperature of the reaction gas mixture increases linearly after exit from the last catalytically active zone viewed in the flow direction and before entry into the heat exchanger over a period of at least 15 minutes.

3. The process according to claim 1, wherein the reactor has two or more catalytically active zones arranged after one another and the point in time after which the conversion does not fluctuate by more than 1%, based on the final conversion, is determined as the point in time after which the increase in temperature of the reaction gas mixture increases to a greater extent on exit from each catalytically active zone compared to the increase in temperature on exit from the immediately preceding catalytically active zone.

4. The process according to claim 1, wherein the production mode of the autothermal gas-phase dehydrogenation is operated until the increase in temperature of the reaction gas mixture, based on the point in time after which the conversion does not fluctuate by more than 1%, based on the final conversion, does not exceed 4 K.

5. The process according to claim 4, wherein the production mode of the autothermal gas-phase dehydrogenation is operated until the increase in temperature of the reaction gas mixture, based on the point in time after which the conversion does not fluctuate by more than 1%, based on the final conversion, does not exceed 3 K.

6. The process according to claim 1, wherein the increase in temperature of the reaction mixture is based on the point in time after which the conversion does not fluctuate by more than 0.5%, based on the final conversion.

7. The process according to claim 6, wherein the increase in temperature of the reaction gas mixture on exit of the latter from the discharge line is based on the point in time after which the conversion does not fluctuate by more than 0.2%, based on the final conversion.

8. The process according to claim 1, wherein not more than 15% of the total operating time is taken up by the regeneration mode in each operating cycle comprising in each case one production mode and one regeneration mode.

9. The process according to claim 8, wherein not more than 10% of the total operating time is taken up by the regeneration mode in each operating cycle comprising in each case one production mode and one regeneration mode.

10. The process according to claim 8, wherein not more than 5%, of the total operating time is taken up by the regeneration mode in each operating cycle comprising in each case one production mode and one regeneration mode.

11. The process according to claim 1, wherein the hydrocarbon-comprising gas stream to be dehydrogenated is introduced into the heat exchanger at two or more places.

12. The process according to claim 1, wherein the hydrocarbon-comprising gas stream to be dehydrogenated is introduced into the heat exchanger at two or more places, as a main stream having a higher mass flow and one or more secondary streams having a lower mass flow than the main stream.

13. The process according to claim 1, wherein one or more additional heating means in addition to the heat exchanger are provided for the hydrocarbon-comprising gas stream to be dehydrogenated.

14. The process according to claim 1, wherein two or more catalytically active zones each having a packing composed of monoliths stacked on top of one another, next to one another and behind one another are provided in the inner region A, where the monoliths within the same catalytically active zone and/or the two or more catalytically active zones each have a different catalytic activity.

15. The process according to claim 1, wherein two or more catalytically active zones each having a packing composed of monoliths stacked on top of one another, next to one another and behind one another are provided in the inner region A, where the monoliths within the same catalytically active zone each have a different catalytic activity and/or the two or more catalytically active zones each have a different catalytic activity.

16. The process according to claim 1, wherein the housing G is configured as a prism and the side walls of the housing G configured as a prism are configured so as to be able to be taken off individually, so that a complete packing or individual monoliths of a packing of a catalytically active zone can be replaced.

17. The process according to claim 1, wherein a reservoir is provided for the reaction gas mixture leaving the reactor via the discharge line.

18. The process according to claim 1, wherein a reservoir is provided for the reaction gas mixture leaving the reactor via the discharge line, after condensation of the reaction gas mixture and before the reaction gas mixture is passed onto a work-up plant.

19. The process according to claim 1, wherein the autothermal gas-phase dehydrogenation is a dehydrogenation of propane, of butane, of isobutane, of butene or of ethylbenzene.

* * * * *